United States Patent
Eubanks et al.

(10) Patent No.: US 6,989,469 B2
(45) Date of Patent: *Jan. 24, 2006

(54) PREPARATION METHOD

(75) Inventors: David Cleve Eubanks, Southport, FL (US); Raymond Lawrence June, Jurong Island (SG); Timothy Michael Nisbet, Amsterdam (NL); Joseph Broun Powell, Houston, TX (US); Marinus Van Zwienen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/648,072

(22) Filed: Aug. 26, 2003

(65) Prior Publication Data

US 2004/0127761 A1    Jul. 1, 2004

(30) Foreign Application Priority Data

Aug. 27, 2002 (SG) .............................. 200205213-2

(51) Int. Cl.
*C07C 1/00* (2006.01)

(52) U.S. Cl. ..................................... 585/319; 585/469

(58) Field of Classification Search ................ 585/319, 585/469
See application file for complete search history.

(56) References Cited

U.S. PATENT DOCUMENTS 5,210,354 A    5/1993    Dubner et al. .............. 585/469

FOREIGN PATENT DOCUMENTS

| EP | 345856 | 12/1989 |
|----|--------|---------|
| EP | 569.248 B1 | 2/1996 |
| GB | 1.239.185 | 7/1971 |
| JP | 8133995 | 5/1996 |

OTHER PUBLICATIONS

International Search Report. dated Dec. 4, 2003.

*Primary Examiner*—Thuan D Dang

(57) ABSTRACT

The invention pertains to a method of preparing styrene or substituted styrene involving (1) converting a mixture containing alkylbenzene hydroperoxide or substituted alkylbenzene hydroperoxide to a mixture containing phenyl alkanol or substituted phenyl alkanol and (2) dehydrating the phenyl alkanol or substituted phenyl alkanol, characterized by oxidizing an alkene to an alkylene oxide in step (1) in the presence of a heterogenous catalyst and dehydrating the phenyl alkanol or substituted phenyl alkanol in step (2) in the presence of a homogenous dehydration catalyst to obtain styrene or substituted styrene.

6 Claims, No Drawings

PREPARATION METHOD

FIELD OF THE INVENTION

The invention pertains to a method of preparing styrene or substituted styrene by converting a mixture of alkylbenzene hydroperoxide or substituted alkylbenzene hydroperoxide to a mixture of phenyl alkanol or substituted phenyl alkanol and dehydrating the phenyl alkanol or substituted phenyl alkanol.

BACKGROUND OF THE INVENTION

A commonly known process in which phenyl alkanol is converted with the help of a catalyst is a process in which propylene oxide and styrene are produced starting from ethylbenzene. In general, such process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl ethanol, and (iii) converting the 1-phenyl ethanol into styrene by dehydration using a suitable dehydration catalyst. Suitable processes are described for example in U.S. Pat. No. 5,210,354. According to this process in both reaction steps (ii) and (iii) a homogenous catalyst was used. A homogeneous molybdenum catalyst was used for step (ii) and homogeneous p-toluene sulfonic acid was used for step (iii). It was found that the preparation of 1-phenyl ethanol led to the presence of heavy by-products in the crude 1-phenylethanol stream. The crude 1-phenylethanol stream was therefore subjected to a distillation step before step (iii). Feed to step (iii) was removed as an overhead product, and a heavy ends stream, containing some styrene precursors, was removed as a bottom product. U.S. Pat. No. 5,210,354 further describes a process for treating this heavy ends stream to recover some styrene precursors.

In JP 8133995 a homogeneous molybdenum catalyst was used for performing step (ii). The advantage claimed for the process described is that the crude 1-phenylethanol stream is not distilled before being fed to step (iii). However, in order to make the stream suitable as feed for step (iii) the stream had to be treated by a caustic water wash at 30 to 180° C. and water washing. This, however, is also an expensive and laborious method.

In PCT application PCT/EP03/03790 (not prepublished), a process is described where a heterogeneous catalyst is used for step (iii). In the epoxidation step (ii) a homogeneous catalyst or a heterogeneous catalyst can be applied.

It would be useful to obtain a method for which no need exists to treat the crude aryl alcohol feed to step (iii) by distilling off the heavy bottoms, or to wash these from the product. Such process would give a substantial commercial benefit over the prior art methods that need expensive distillation or washing steps. It would be a further advantage not to separate heavies as waste, since this heavy end stream contains valuable styrene precursors. Thus, by using a process without distillation or washing the heavy bottoms, an increase in the yield of valuable products can be obtained.

SUMMARY OF THE INVENTION

The present invention is directed to a process of preparing styrene or substituted styrene comprising (a) converting a mixture comprising alkylbenzene hydroperoxide or substituted alkylbenzene hydroperoxide to a mixture comprising phenyl alkanol or substituted phenyl alkanol by oxidizing an alkene to an alkylene oxide in the presence of a heterogenous catalyst and (b) reacting the phenyl alkanol or substituted phenyl alkanol product of step (a) to obtain styrene or substituted styrene in the presence of a homogeneous dehydration catalyst. More specifically, the process includes a method of preparing a mixture comprising propylene oxide and 1-phenylethanol (also known as alpha-phenyl ethanol or methyl phenyl carbinol) or substituted 1-phenyl ethanol and subsequently dehydrating 1-phenylethanol or substituted 1-phenylethanol to styrene or a substituted styrene.

DETAILED DESCRIPTION OF THE INVENTION

In a preferred embodiment, the method comprises oxidizing ethylbenzene and reacting the resulting mixture containing ethylbenzene hydroperoxide with propene in step (1) using a heterogeneous catalyst to obtain a mixture comprising propylene oxide and 1-phenylethanol.

Heterogenous catalysts can be selected from catalysts containing titanium, zirconium, molybdenum and/or vanadium compounds. Catalysts containing titanium and/or zirconium and silica, are preferred. A particularly suitable heterogenous catalyst is a catalyst containing titanium and silica, more specifically a catalyst as described in EP-A-345856 herein incorporated by reference.

Conditions under which epoxidation is carried out are known in the art and include temperatures of 75° C. to 150° C. and pressures up to 80 bar. The reaction medium is preferably in the liquid phase.

After the epoxidation step, unreacted propene, propylene oxide product and ethyl benzene solvent are separated from the crude 1-phenylethanol stream. The crude phenylethanol stream is fed directly to the second, dehydration, step. This reaction is performed in the presence of a homogeneous catalyst. Preferred homogeneous catalysts are inorganic or organic acids, such as p-toluene sulfonic acid. According to the present process it is no longer required to subject the effluent from the epoxidation step (1) to a separation treatment to remove heavy components before feeding the crude 1-phenylethanol stream to the dehydration step (2). Heavy components which are especially preferred to be present, are compounds having a molecular weight of 195 or higher, more specifically 200 or higher. It was found that the presence of these heavy compounds resulted in the preparation of a relatively large amount of styrene or substituted styrene, based on amount of starting compounds used in the process.

The invention is further illustrated by the following examples.

EXAMPLE 1

In a reactor, air was blown through ethylbenzene. The product contained ethylbenzene hydroperoxide.

The product obtained was reacted with propene in the presence of a heterogeneous titanium on silica catalyst as described in the Example according to EP-A-345856. Unconverted ethylbenzene and propylene oxide were removed from the product, and a crude 1-phenylethanol feed was obtained. This crude 1-phenylethanol stream had the following composition:

| | |
|---|---|
| 1-phenylethanol | 77.6 wt. % |
| 2-phenylethanol | 3.5 wt. % |
| acetophenone | 11.8 wt. % |
| 2,3-diphenylethyl ether | 0.7 wt. % |
| Other heavy components with boiling points above 2,3-diphenylethyl ether | 1.3 wt. % | p-Toluene sulfonic acid was added to the crude 1-phenylethanol stream at a level of 200 ppmw (parts per million weight), and dehydration was carried out continuously in the liquid phase at 218° C., 0.2 bar and at a throughput of 0.34 (g feed) per (g reaction liquid) per h. Crude styrene and water products were removed as vapor and condensed. The styrene concentration in the product was determined by gas chromatography. The amount of heavy residue produced was 4.4 wt. % on styrene produced.

EXAMPLE 2

A crude 1-phenylethanol stream was prepared as in Example 1. This was further treated by distillation, according to PCT application PCT/EP03/03790, so that the majority of heavy compounds were removed. The resulting stream had the following composition:

| | |
|---|---|
| 1-phenylethanol | 80.9 wt. % |
| 2-phenylethanol | 3.7 wt. % |
| acetophenone | 9.8 wt. % |
| 2,3-diphenylethyl ether | 0.02 wt. % |
| Other heavy components with boiling points above 2,3-diphenylethyl ether | not detected | p-Toluene sulfonic acid was added to the crude 1-phenylethanol stream at a level of 200 ppmw, and dehydration was carried out continuously in the liquid phase at 218° C., 0.2 bar and at a throughput of 0.39 (g feed) per (g reaction liquid) per h. Crude styrene and water products were removed as vapour and condensed. The styrene concentration in the product was determined by gas chromatography. The amount of heavy residue produced was 3.0 wt. % on styrene produced. The total of this heavy residue plus the heavy residue removed in the prior distillation step (0.7 wt. % of 2,3-diphenylethyl ether and 1.3 wt. % of other heavy components with boiling points above 2,3-diphenylethyl ether) exceeded the total heavy residue formed in Example 1.

EXAMPLE 3

The crude 1-phenylethanol stream from Example 1 was treated as follows: p-toluene sulfonic acid was added to the crude 1-phenylethanol stream at a level of 200 ppmw, and dehydration was carried out continuously in the liquid phase at 238° C., 0.2 bar and at a throughput of 0.19 (g feed) per (g reaction liquid) per h. Crude styrene and water products were removed as vapour and condensed. The styrene concentration in the product was determined by gas chromatography. The amount of heavy residue produced was 2.3 wt. % on styrene produced.

EXAMPLE 4

The distilled 1-phenylethanol stream from Example 2 was treated as follows: p-Toluene sulfonic acid was added to the crude 1-phenylethanol stream at a level of 200 ppmw, and dehydration was carried out continuously in the liquid phase at 239° C., 0.2 bar and at a throughput of 0.31 (g feed) per (g reaction liquid) per h. Crude styrene and water products were removed as vapour and condensed. The styrene concentration in the product was determined by gas chromatography. The amount of heavy residue produced was 1.6 wt. % on styrene produced. The total of this heavy residue plus the heavy residue removed in the prior distillation step (0.7 wt. % of 2,3-diphenylethyl ether and 1.3 wt. % of other heavy components with boiling points above 2,3-diphenylethyl ether) exceeded the total heavy residue formed in Example 3.

We claim:

1. A method of preparing styrene or substituted styrene comprising:
   (a) converting a mixture comprising alkylbenzene hydroperoxide or crude substituted alkylbenzene hydroperoxide and an alkene to a mixture comprising a crude phenyl alkanol or crude substituted phenyl alkanol and an alkylene oxide in the presence of a heterogeneous catalyst; and
   (b) dehydrating the crude phenyl alkanol or substituted phenyl alkanol or substituted phenyl alkanol in the presence of a homogeneous dehydration catalyst to obtain styrene or substituted styrene.

2. The method of claim 1, which is preceded by a non-catalyzed step wherein alkylbenzene or substituted alkylbenzene is oxidized to a mixture comprising alkylbenzene hydroperoxide or substituted alkylbenzene hydroperoxide.

3. The method of claim 1 in which the alkylbenzene hydroperoxide comprises ethylbenzene hydroperoxide and the phenyl alkanol comprises 1-phenylethanol.

4. The method of claim 3 in which the heterogeneous catalyst is selected from the group consisting of supported titanium compounds, zirconium compounds, molybdenum compounds, vanadium compounds, and the homogeneous catalyst is selected from the group consisting of inorganic acids and organic compounds.

5. The method of claim 1 in which the heterogeneous catalyst comprises titanium on silica, and the homogeneous catalyst comprises an aromatic and/or sulfonic acid.

6. The method of claim 5, in which the homogeneous catalyst comprises p-toluene sulfonic acid.

* * * * *